US009098988B2

(12) United States Patent
Ju et al.

(10) Patent No.: US 9,098,988 B2
(45) Date of Patent: Aug. 4, 2015

(54) INTEGRATED SMOKE CELL

(71) Applicant: Excelitas Canada, Inc., Vaudreuil-Dorion (CA)

(72) Inventors: Jin Han Ju, Kirkland (CA); Arthur John Barlow, Alton (GB)

(73) Assignee: Excelitas Technologies Philippines Inc., Cabuyao (PH)

( * ) Notice: Subject to any disclaimer, the term of this patent is extended or adjusted under 35 U.S.C. 154(b) by 175 days.

(21) Appl. No.: 13/717,849

(22) Filed: Dec. 18, 2012

(65) Prior Publication Data

US 2014/0168647 A1    Jun. 19, 2014

(51) Int. Cl.
G01N 21/00      (2006.01)
G08B 17/107   (2006.01)
G01N 21/53      (2006.01)

(52) U.S. Cl.
CPC .............. G08B 17/107 (2013.01); G01N 21/53 (2013.01); *Y10T 29/49002* (2015.01); *Y10T 29/4998* (2015.01); *Y10T 29/49826* (2015.01)

(58) Field of Classification Search
USPC ......... 356/337, 338, 438, 439, 432–437, 440;
250/574, 576; 340/286.05, 628, 630
See application file for complete search history.

(56) References Cited

U.S. PATENT DOCUMENTS

| 4,306,230 | A | * | 12/1981 | Forss et al. ..................... 340/630 |
| 4,596,465 | A | | 6/1986 | Nagashima |
| 5,283,816 | A | * | 2/1994 | Gomez Diaz ................... 379/40 |
| 5,400,014 | A | * | 3/1995 | Behlke et al. .................. 340/630 |
| 5,719,557 | A | * | 2/1998 | Rattman et al. ............... 340/628 |
| 6,914,535 | B2 | * | 7/2005 | Matsukuma et al. ......... 340/630 |
| 7,978,087 | B2 | * | 7/2011 | Siber et al. ..................... 340/630 |
| 2006/0202847 | A1 | * | 9/2006 | Oppelt et al. .................. 340/630 |
| 2008/0297361 | A1 | * | 12/2008 | Cole et al. ...................... 340/630 |

FOREIGN PATENT DOCUMENTS

| EP | 1049060 | A2 | 11/2000 |
| GB | 2000282 | A | 1/1979 |
| GB | 2170597 | A | 8/1986 |

OTHER PUBLICATIONS

International Search Report and Written Opinion for PCT/US2013/074947, dated Feb. 28, 2014.
Drawing and Description of Proprietary Smoke Cells, Prior Art Fig 2. (2005).
Drawing and Description of Proprietary Smoke Cells, Prior Art Fig 3. (Oct. 2012).

* cited by examiner

*Primary Examiner* — Hoa Pham
(74) *Attorney, Agent, or Firm* — Peter A. Nieves; Sheehan Phinney Bass + Green PA

(57) ABSTRACT

A device and method for manufacturing an integrated smoke cell are presented. The smoke cell includes an integral housing with a ceiling portion and a smoke permeable wall forming a chamber when mounted on a printed circuit board. An emitter and detector are mounted above apertures in the chamber ceiling so the emitter and detector are mounted substantially outside the chamber while detecting smoke present within the chamber without blocking ingress of smoke through the chamber wall.

20 Claims, 11 Drawing Sheets

INTEGRATED SMOKE CELL

FIELD OF THE INVENTION

The present invention relates to semiconductor devices and more particularly, is related to a circuit board mounted smoke sensor.

BACKGROUND OF THE INVENTION

Smoke sensors generally sense the presence of smoke within a chamber between an emitter and a detector. FIG. 1A is a schematic diagram of a first prior art smoke detector 100. Smoke particles enter an optical chamber 130. The chamber is mounted on a case molding 137, and covered by a cover 135. The smoke enters the optical chamber through a series of baffles 170. The baffles are shaped to allow ingress of smoke into the optical chamber, but to block direct ingress of light from nearby light sources. Smoke particles in the path of an emitter 120 are illuminated by light produced by the emitter 120, and the illuminated smoke particles scatter the light which is then detected by the detector 110. The emitter 120 and detector 110 are located inside the optical chamber. FIG. 1B is a simplified diagram of the prior art smoke detector, showing an angle α between the orientation of the detector 110 and the emitter 120. The emitter 120 and detector 110 are oriented at the angle α to prevent light emitted from the emitter 120 from projecting directly into the detector 110. The angle α is typically on the order of 135 degrees. Therefore, the detector 110 will only detect light from the emitter 120 when the emitted light is scattered in a diffuse manner by discrete smoke particles within the chamber 130. However, since the emitter 120 and detector 110 are physically located within the chamber 130, as shown by FIG. 1C, they may block the ingress of smoke entering the chamber 130 from some directions, thereby increasing the detection time.

It should be noted that many constraints are placed on the designs of smoke cells by regionally specific manufacturing and/or usage standards documents, for example, Deutsche Norm Din En 14604.

FIG. 2 shows a second prior art smoke cell 200, where a smoke chamber 230 is formed by a housing having series of baffles 270 and a ceiling 260, mounted directly to a printed circuit board (PCB) 250. An emitter 220 and a detector 210 are mounted to an optic block 240, where the optic block 240 is mounted to the PCB 250, inside the smoke chamber 230. The optic block 240 is configured so the angle between the emitter 220 and the detector 210 may be on the order of 135 degrees. However, the location of the optic block 240 within the smoke chamber 230 may physically block smoke from entering the smoke chamber 230.

Therefore, there is a need in the industry to address the shortcomings described above.

SUMMARY OF THE INVENTION

Embodiments of the present invention provide an integrated smoke cell and a method for manufacturing an integrated smoke cell. Briefly described, the present invention is directed to an integrated smoke cell having an integral housing including a ceiling portion and a smoke permeable wall portion, the housing substantially defining a chamber within the housing. An emitter is mounted substantially above a first aperture in the ceiling, the emitter having an emitting region adjacent to the emitter disposed within the chamber. A detector is mounted substantially above a second aperture in the ceiling, the detector having a detecting region adjacent to the detector disposed within the chamber and at least partially intersecting the emitting region. The emitter and detector are disposed substantially outside the chamber.

A second aspect of the present invention is directed to a smoke cell configured to be mounted on a circuit board including an integral housing having a ceiling portion and a wall portion. The housing substantially defines a chamber within the housing. The wall has a plurality of spaced baffles disposed adjacent to the ceiling, a first emitter mounted substantially above a first emitter aperture in the ceiling, a second emitter mounted substantially above a second emitter aperture in the ceiling, and a first detector mounted substantially above a first detector aperture in the ceiling. The first emitter, the second emitter and the first detector are disposed substantially outside the chamber.

Briefly described, in architecture, a third aspect of the present invention is directed to an integrated smoke cell housing. The integrated smoke cell housing includes a ceiling portion having a first component mount disposed on a first ceiling side substantially above a first aperture in the ceiling, and a second component mount disposed on the first ceiling side substantially above a second aperture in the ceiling, and a smoke permeable wall portion having a series of spaced baffles mounted substantially around a perimeter of a second side of the ceiling. The first and second component mount are configured to receive and position a first component and a second component.

A fourth aspect of the present invention is directed to a method for manufacturing an integrated smoke cell having the step of forming an integral housing having a ceiling portion having a first component mount disposed on an exterior ceiling side substantially above a first aperture in the ceiling, and a second component mount disposed on the exterior ceiling side substantially above a second aperture in the ceiling and a smoke permeable wall portion having a series of spaced baffles mounted substantially around a perimeter of an interior side of the ceiling. The first component mount is configured to receive and position a first component and the second component mount is configured to receive and position a second component.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principals of the invention.

DETAILED DESCRIPTION

Figure 1A:
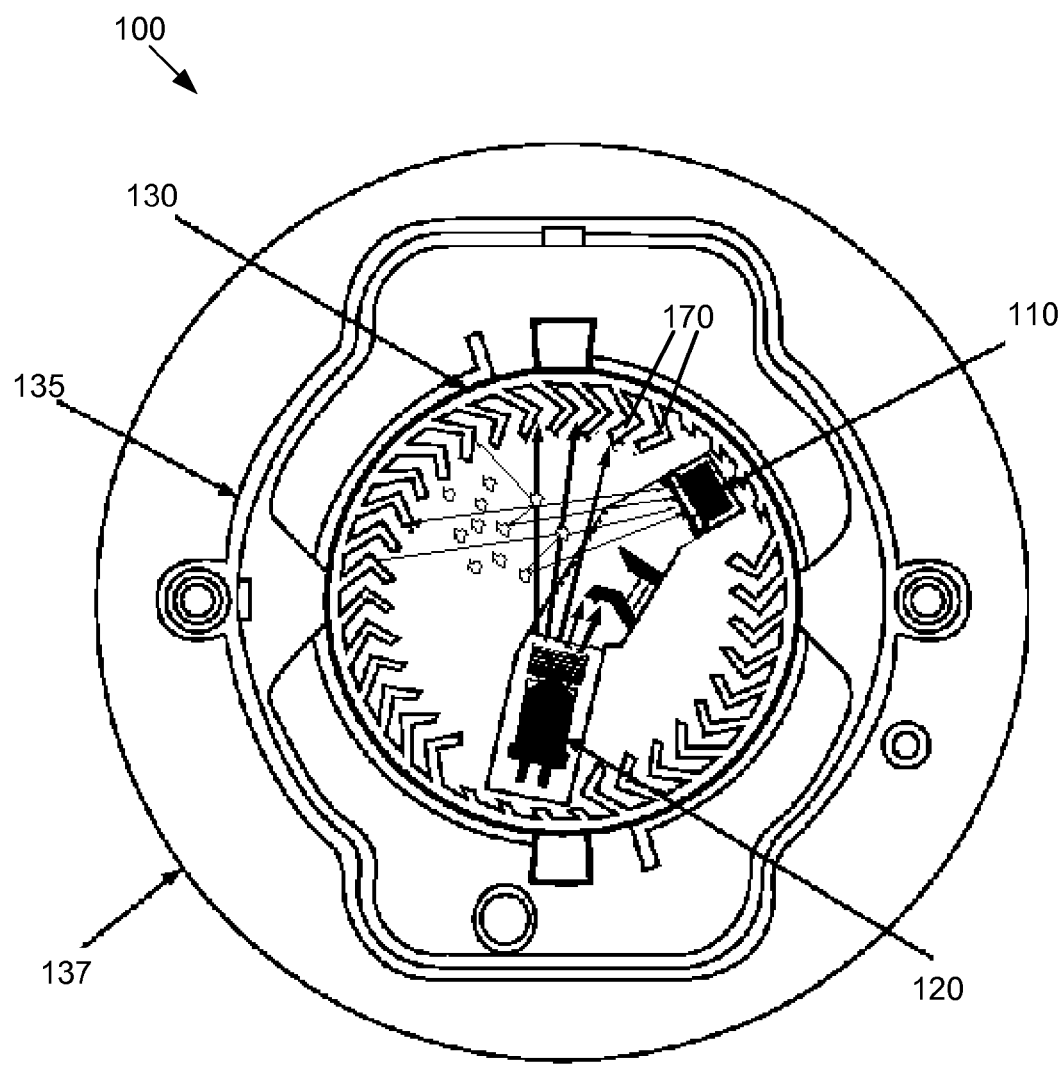
FIG. 1A is a schematic diagram of a top view a first prior art smoke detector.
Figure 1B:
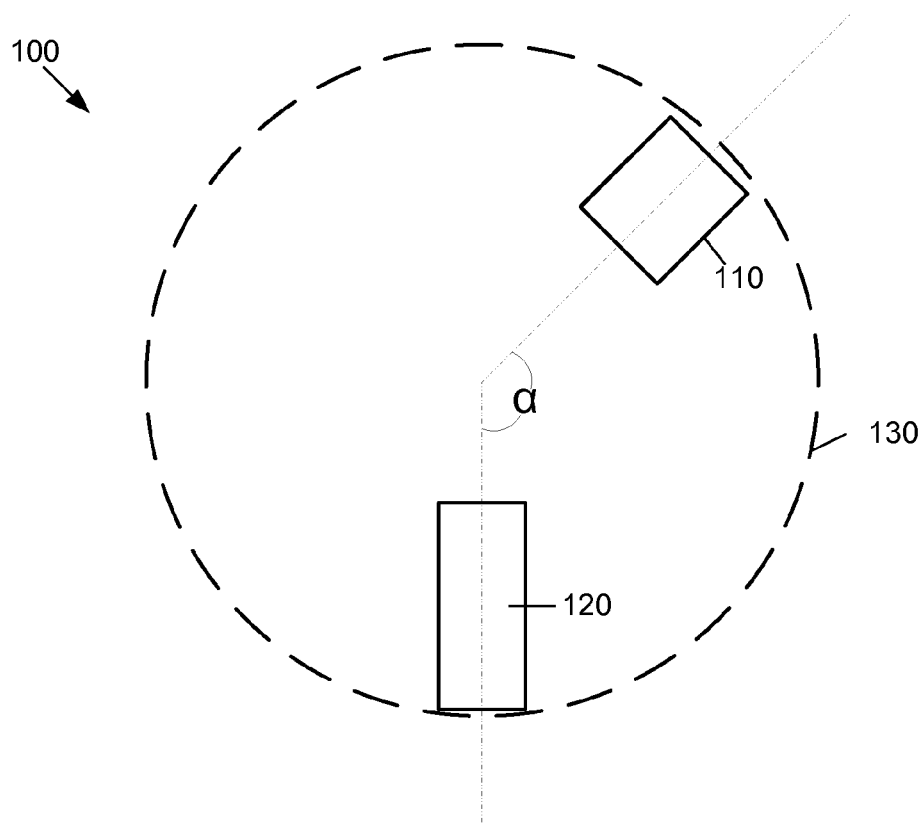
FIG. 1B is a simplified schematic diagram of the top view the first prior art smoke detector.
Figure 1C:
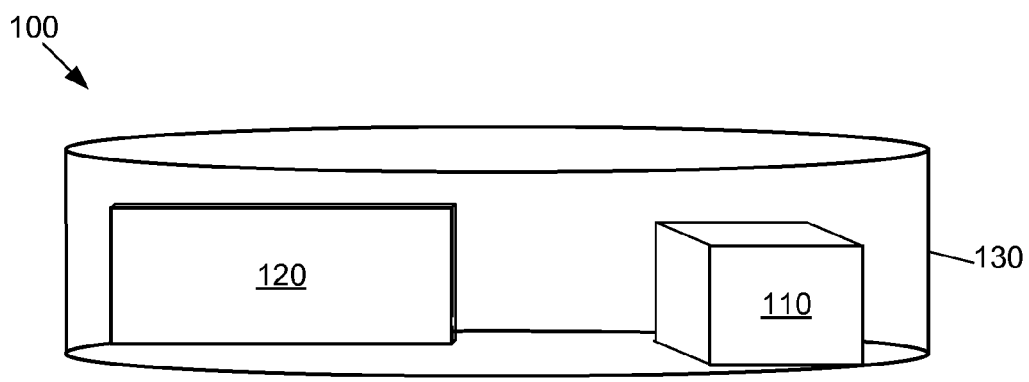
FIG. 1C is a simplified schematic diagram of a side view the first prior art smoke detector.
Figure 2:
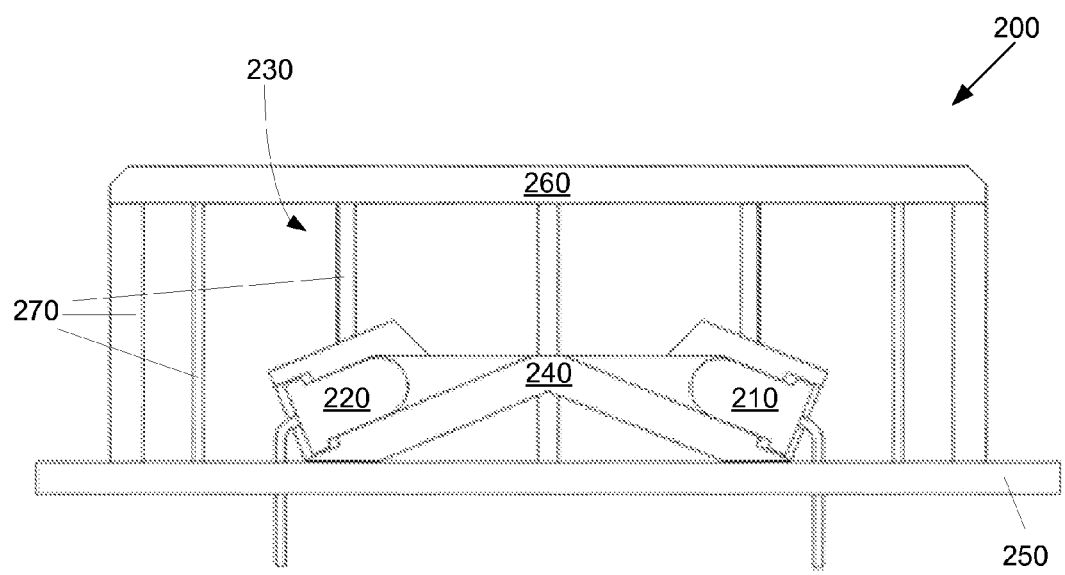
FIG. 2 is a schematic diagram of a second prior art smoke cell.

Reference will now be made in detail to embodiments of the present invention, examples of which are illustrated in the accompanying drawings. Wherever possible, the same reference numbers are used in the drawings and the description to refer to the same or like parts.

As mentioned previously, the presence of emitting and sensing components within a smoke chamber in prior art smoke cells may at least partially block ingress of smoke into the smoke chamber. An object of the current invention is a smoke cell having emitters and detectors physically located outside the smoke chamber. A second object for the current invention is a smoke cell having all components mounted on the same side of a PCB. A third object of the current invention is a one piece smoke chamber housing that may be formed by injection molding. A fourth object of the current invention is a smoke cell configured to detect different types of smoke particles without obstructing smoke ingress into the smoke chamber.

First Embodiment

Figure 3:
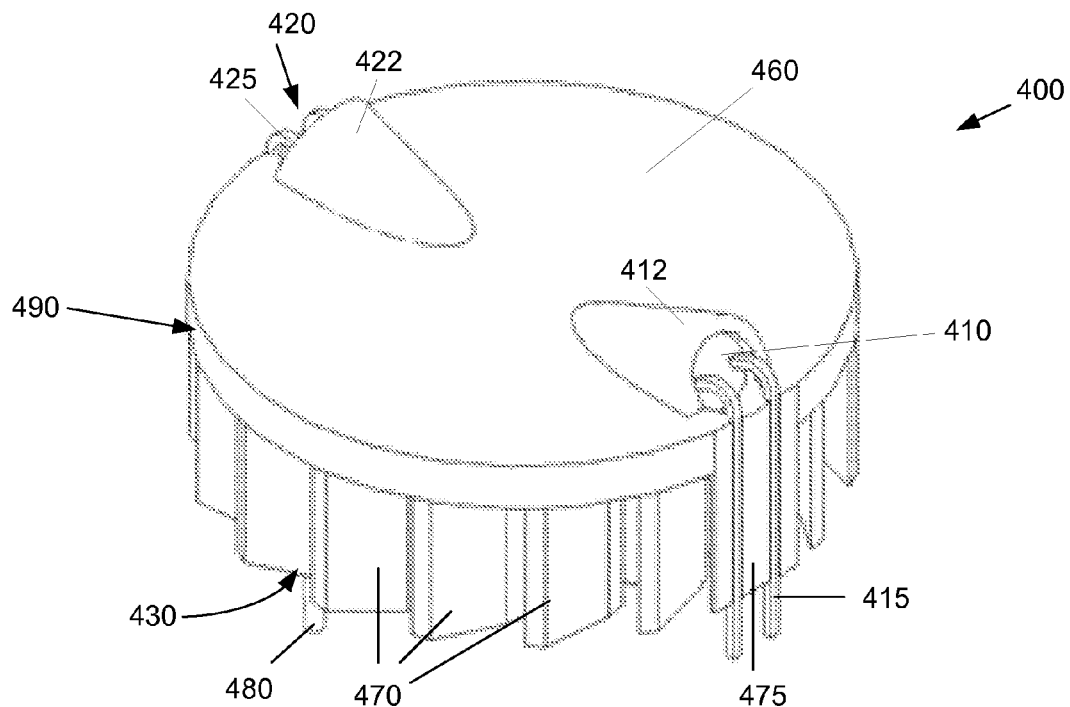
FIG. 3 is a perspective view of the top side of an exemplary first embodiment of the integrated smoke cell.

FIG. 3 shows a first exemplary embodiment of an integrated smoke cell 400 under the present invention. The integrated smoke cell 400 includes an integral housing 490 including a ceiling 460 and a side wall formed of a series of baffles 470. A smoke chamber 430 is formed within the housing 490, bounded by the ceiling 460 and side wall, and further bounded by a PCB (not shown) forming a floor of the smoke chamber 430. Under the first embodiment, the side wall formed of a series of baffles 470 is substantially circular in shape. However, there is no objection to a side wall having other shapes, for example, a substantially square shape, as long as the ability of smoke to enter the chamber 430 is substantially the same from all directions around the perimeter of the side wall.

The side wall is formed by the series of baffles 470. Each baffle 470 is shaped to be aligned with an adjacent baffle 470 such that a vent is formed between each adjacent baffle 470 allowing smoke to enter the chamber 430 through the vent. The baffles 470 are arranged such that a direct beam of light cannot enter the chamber 430 through the vent. Under the first embodiment, the baffles 470 have a lambda ($\lambda$) shaped profile, such that the stem portion of a first lambda shaped baffle 470 extends into a space beneath a second lambda shaped baffle 470, leaving enough space for smoke to traverse the vent, but blocking direct light from entering the chamber 430 through the vent. The orientation of the lambda baffle stem pointing into the chamber 430 may facilitate ingress of smoke into the chamber 430.

Figure 4:
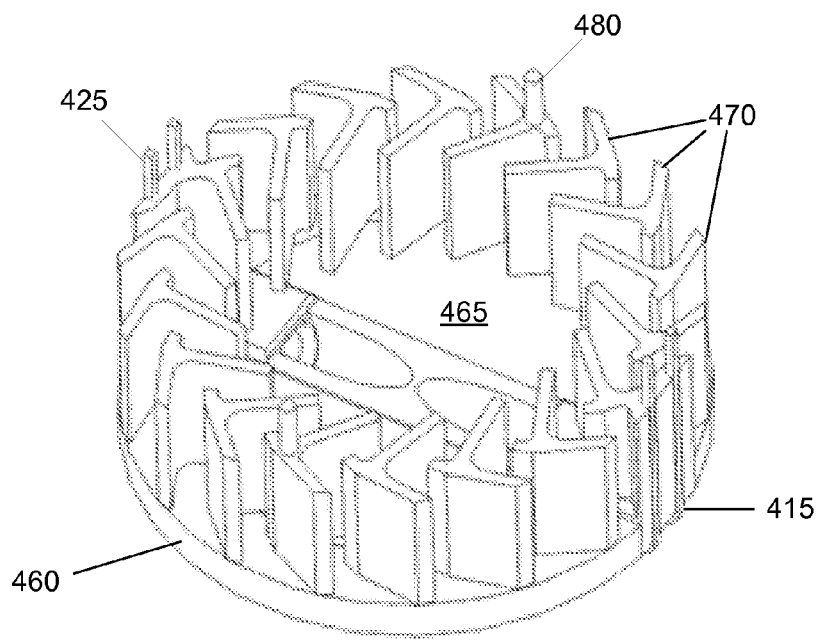
FIG. 4 is a perspective view of the underside of the exemplary first embodiment of the integrated smoke cell.
Figure 5:
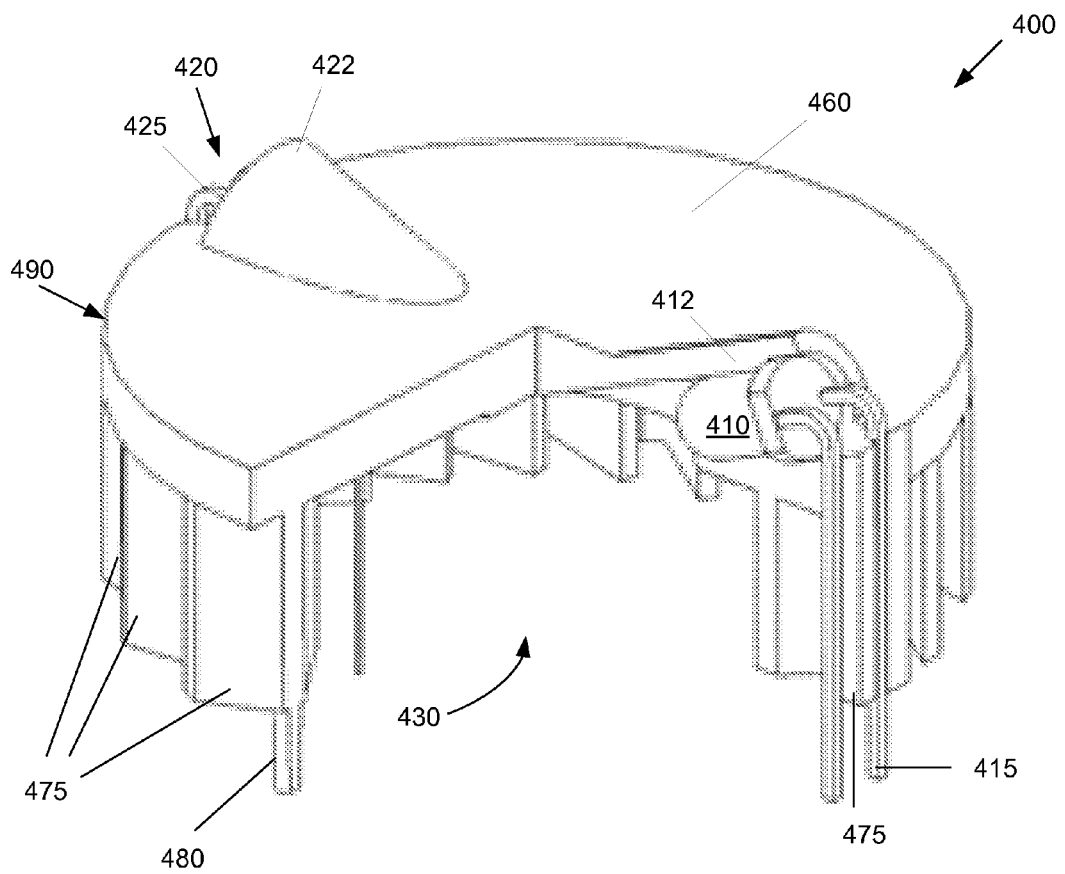
FIG. 5 is a cutaway perspective view of the exemplary first embodiment of the integrated smoke cell.

As shown by FIG. 4, the inner surface of the ceiling 460 within the chamber 430 may preferably be treated to disperse and/or absorb light within the chamber 430. For example, the surface may be textured or patterned to disperse and/or absorb light. Similarly, the surface may be coated with a substance that disperses and/or absorbs light. The ceiling 460 includes an emitter aperture and an adjacent emitter mount 422 (FIG. 5) configured to receive an emitter 420. The emitter 420 emits light of a wavelength chosen to illuminate smoke particles. The emitter 420 may be, for example, a light emitting diode (LED). As shown in FIG. 5, the emitter 420 is mounted within the emitter mount 422 such that the emitter 420 is positioned to emit a light beam into the smoke chamber 430 without having the emitter 420 itself physically intruding into the smoke chamber 430. Similarly, the ceiling 460 includes a detector aperture and an adjacent detector mount 412 configured to receive a detector 410. The detector 410 is mounted within the detector mount 412 such that the detector 410 is configured to detect light within the smoke chamber 430 without having the detector 410 itself physically intruding into the smoke chamber 430. The detector 410 may be, for example, a photodiode.

Figure 6:
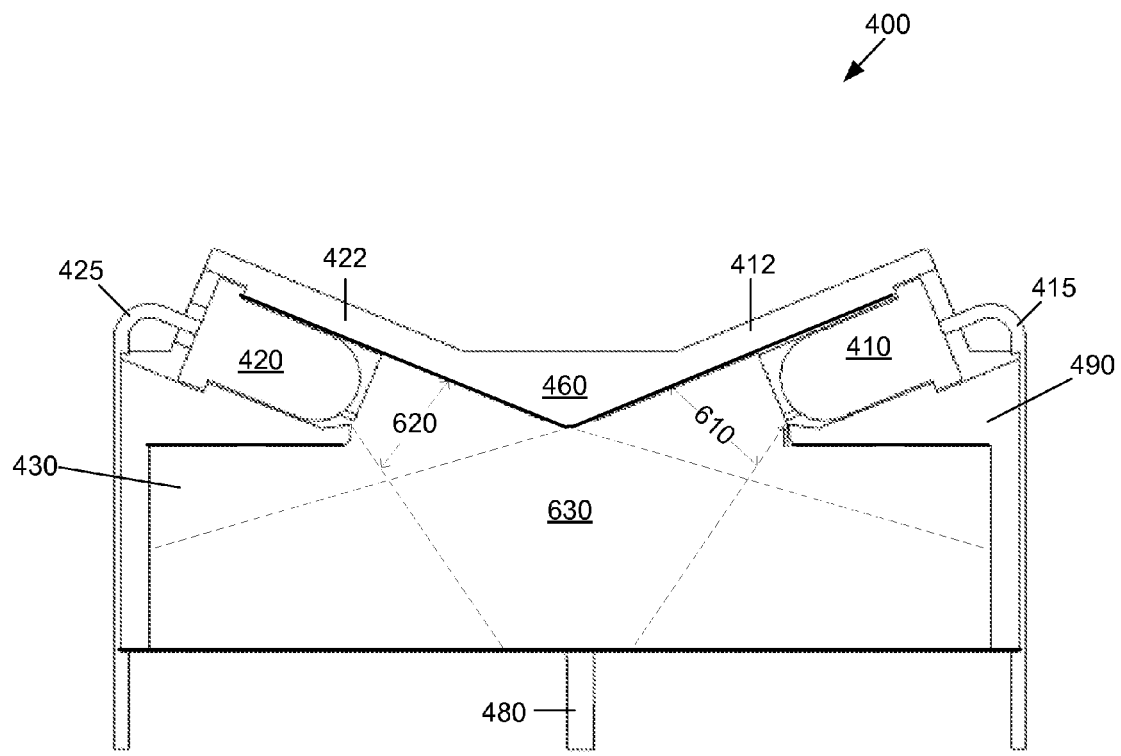
FIG. 6 is a schematic diagram of a sectional side view of the interior of the exemplary first embodiment of the integrated smoke cell detailing the interference zone.

As shown by FIG. 6, the emitter 420 emits one or more light beams in a light path 620 in front of an emitting end of the emitter 420. The detector 410 detects light within a detection region 610 in front of a detecting end of the detector 410. The emitter 420 and detector 410 are oriented at an angle $\alpha$ (FIG. 7) with respect to the ceiling 460 such that emitter 420 light path 620 intersects with the detection region 610 of the detector 410. This area of intersection is called the interference zone 630. Smoke within the interference zone 630 is illuminated by light from the emitter 420, so that illuminated smoke particles within the interference zone 630 may scatter light to be detected by the detector 410. Smoke may be declared to be present within the smoke chamber when the intensity of light detected by the detector 410 meets and/or exceeds an illumination threshold.

Figure 7:
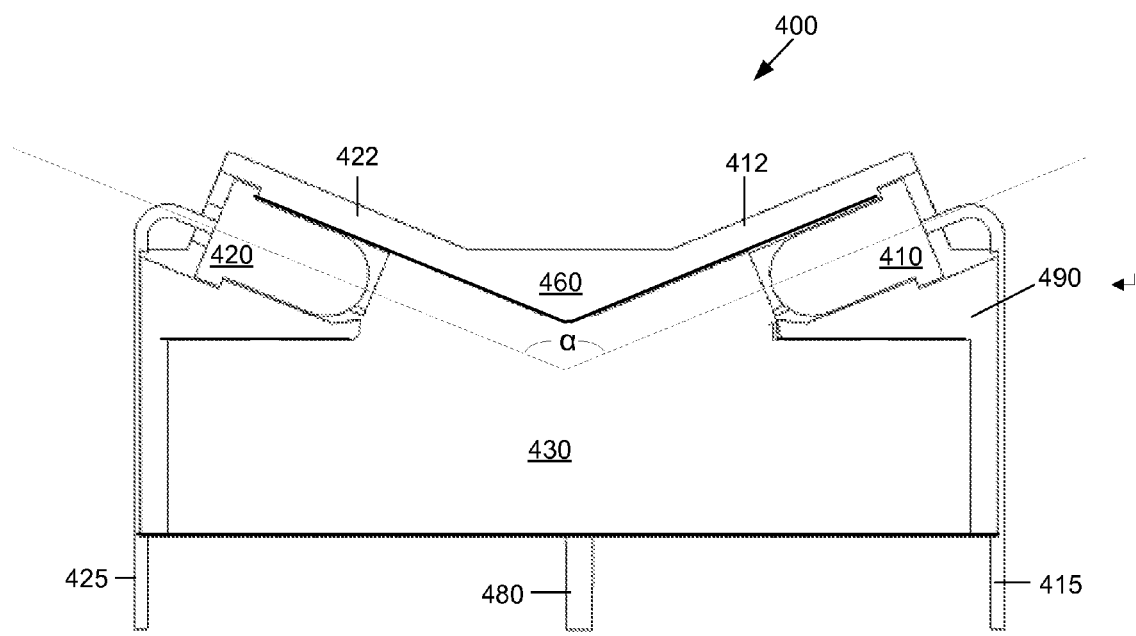
FIG. 7 is a schematic diagram side view of the interior of the exemplary first embodiment of the integrated smoke cell detailing the relative angle between the emitter and the detector.

By locating the emitter 420 and detector 410 in the ceiling 460, the interference zone may be positioned within the chamber 430, so that the emitter 420 and detector 410 do not physically obstruct ingress of smoke into the chamber 430 through vents between the baffles 470 (FIG. 5). In alternative embodiments, the emitter 420 and detector 410 may partially protrude through the ceiling 460 into the chamber 430. The emitter 420 and the detector 410 are positioned so the light beam path of the emitter 420 does not project directly into the detector 410. As shown by FIG. 7, the emitter 420 is oriented at an angle $\alpha$ relative to the detector 410, where the angle is generally mandated by fire safety standards. The angle $\alpha$ may be, for example, approximately 135 degrees. However, there is no objection to other angles.

The emitter mount 422 may be shaped to receive a selected emitter 420 and the detector mount 412 may be shaped to receive a selected detector 410 such that the emitter 420 and detector 410 are located and oriented at the desired angle $\alpha$ to form an interference zone 630 (FIG. 6) of the desired proportions and location within the chamber 430. The emitter mount 422 and detector mount 412 may be substantially tube shaped both to accommodate the shapes of the emitter 420 and detector 410 and to guide the emitter 420 and detector 410 into desired mounting positions.

Returning to FIG. 5, the detector 410 may include electrical detector leads 415. The emitter 420 may include electrical emitter leads 425. The electrical leads 415, 425 may be electrically connected to the printed circuit board the integrated smoke cell 400 is mounted to. The printed circuit board electrically connects the integrated smoke cell 400 with other components in a smoke detector system 1000 (FIG. 10), described below. The electrical leads 415, 425 may be configured to electrically connect to the printed circuit board, for example, as through-hole leads, or as surface mount leads. It is desirable that the electrical leads 415, 425 do not block ingress of smoke into the chamber 430. To this end a modified baffle 475 may be used in proximity to the electrical leads 415, 425. The modified baffle 475 may secure the electrical leads 415, 425 within holes, slots, or ridges in the modified baffle 475. In alternative embodiments the electrical leads 415, 425 may share a single modified baffle 475, or be electrically connected to produce a single pair of leads combining the leads for any number of emitters 420 and detectors 410 to minimize obstruction of airflow into the chamber 430.

The integral one-piece housing 490 includes the baffles 470, ceiling 460, and apertures for receiving the emitter 420 and detector 410. The housing 490 may also include one or more guide features, such as positioning pins 480. The guide features may be used to orient the housing 490 in relation to a PCB the housing 490 is mounted upon. The positioning pins 480 may pass through apertures in the PCB, extending through a far side of the PCB in relation to a near side of the PCB where the housing 490 is mounted. The housing 490 is formed as one piece of material. The material may be, for example, plastic or metal. A plastic smoke detector housing 490 may be formed by injection molding. It may be desirable for the housing to have a melting point above the melting point of solder, so the housing remains intact while components, for example, the emitter 420 and detector 410 are soldered to the PCB. For a plastic housing 490, a portion of the mounting pins extending through and past the far side of the PCB may be melted to secure the housing 490 to the PCB. In alternate embodiments, the guide features may be formed as tabs or ridges that are secured by, for example, holes, troughs or ridges in the PCB. Similarly, other alternative embodiments may provide for the smoke cell 400 to be attached to a PCB using surface mount device (SMD) techniques. For example, electrical leads 415 may be bent so that a portion of the leads are parallel to the plane of the PCB to allow them to lie flat onto the PCB and thereby be soldered using, for example, solder paste and reflow methods.

Second Embodiment

Figure 8:
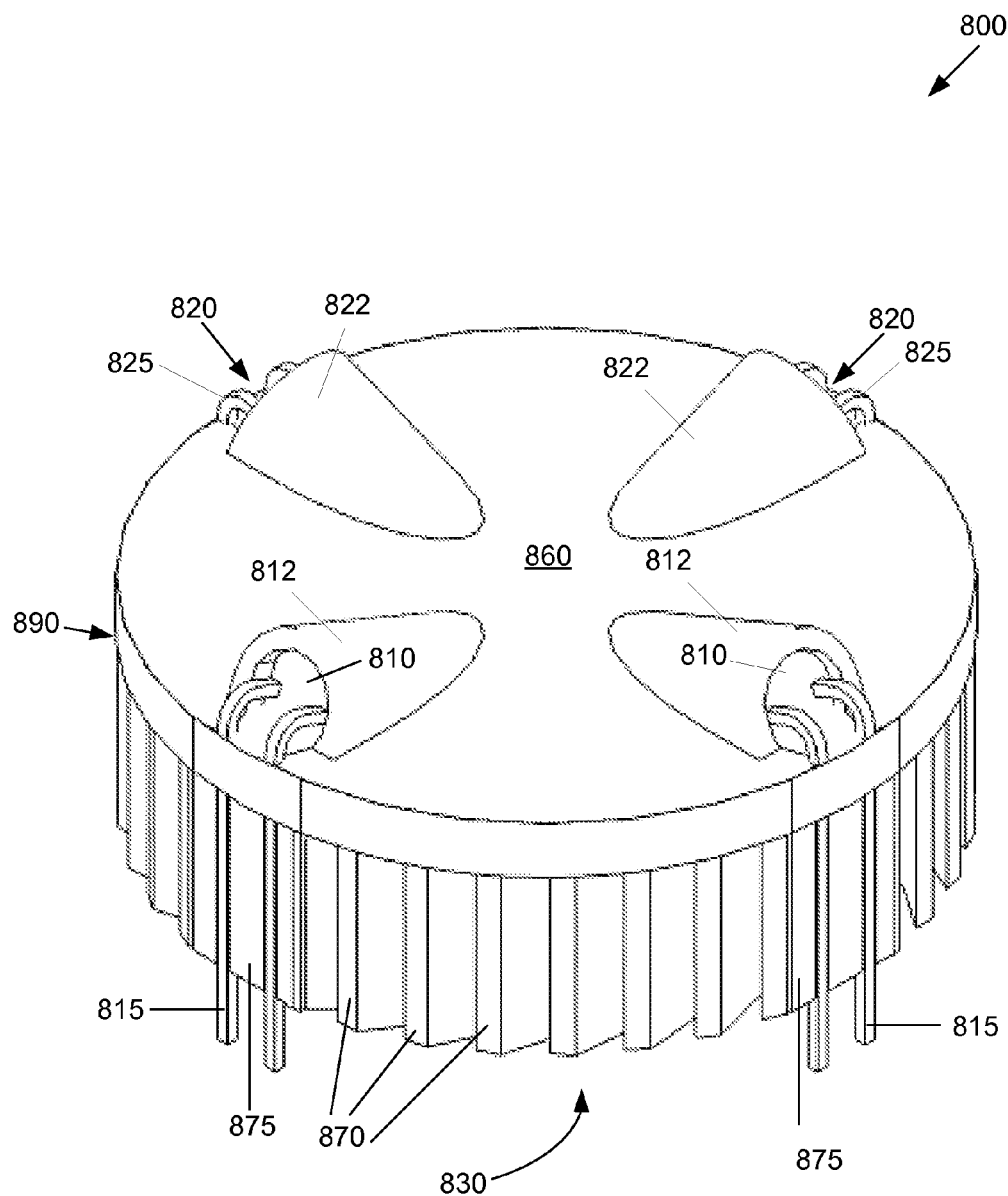
FIG. 8 is a perspective view of the top side of an exemplary second embodiment of the integrated smoke cell.

FIG. 8 shows a second exemplary embodiment of an integrated smoke cell 800. The smoke cell 800 has an integral one piece housing 890 including a ceiling 860 and side wall formed from a series of spaced baffles 870. The housing 890 is configured to be mounted to a PCB (not shown), such that the ceiling 860, side wall and PCB form a smoke chamber 830. Smoke may enter the chamber 830 through vents between the baffles 870. The ceiling 860 has apertures formed to permit chamber 830 access to one or more emitters 820, and one or more detectors 810 mounted outside the chamber 830. The second embodiment as shown in FIG. 8 includes two emitters 820, and two detectors 810. An emitter 820 and a detector 810 may be paired, such that the emitter 820 is positioned substantially diametrically opposite across the ceiling 860 from the detector 810. Emitters 820 and detectors 810 are configured to be mounted in the ceiling 860 so they either do not physically protrude into the chamber 830, or so they only minimally physically protrude into the chamber 830, thereby not interfering or minimally interfering with the ingress of smoke into the chamber 830. The emitters 820 may be mounted in emitter mounts 822, and the detectors 810 may be mounted in detector mounts 810, wherein the emitter mounts 822 and detector mounts 812 are integrally formed with the ceiling 860.

The smoke detector 800 shown in FIG. 8 has two emitter-detector pairs. Each emitter-detector pair may be configured to emit and detect the same wavelength or range of wavelengths, or each emitter-detector pair may be configured to operate on different wavelengths or wavelength ranges. A first pair may be configured to emit and detect a first wavelength selected to detect a first type of smoke, and a second pair may be configured to emit and detect a second wavelength selected to detect a second type of smoke. For example, For example, the first pair may be operate with a first wavelength to detect black smoke resulting from burning materials, while the second pair may be operate with a second wavelength to detect white smoke, which may result from frying food. Other pairs may be tuned to wavelengths for different purposes, for example, to detect steam, chemical smoke, or dust particulates, or other particles.

The interference zones of each emitter-detector pair may be configured to intersect, as shown in FIG. 8, or they may be configured to be substantially independent, for example, if the emitter-detector pairs are configured in parallel alignment. A single emitter 820 may be configured to form an interference zone with two or more detectors 810. The single emitter 820 may produce light having one wavelength, two wavelengths, or a range of wavelengths. Similarly, a single detector 810 may be configured to form an interference zone with two or more emitters 820. A single detector 810 may be configured to detect a single wavelength, multiple wavelengths, or a range of wavelengths. Alternative embodiments may vary the number of emitters 820, the number of detectors 810, and the ratio of the number of emitters 820 to detectors 810. Emitters 820, detectors 810, and emitter-detector pairs may be configured to operate concurrently or at separate times, for example, according to a duty cycle. In addition, other electronic components may be housed within the integrated smoke cell, for example, an ASIC, and assembled on the plastic housing.

Method

Figure 9:
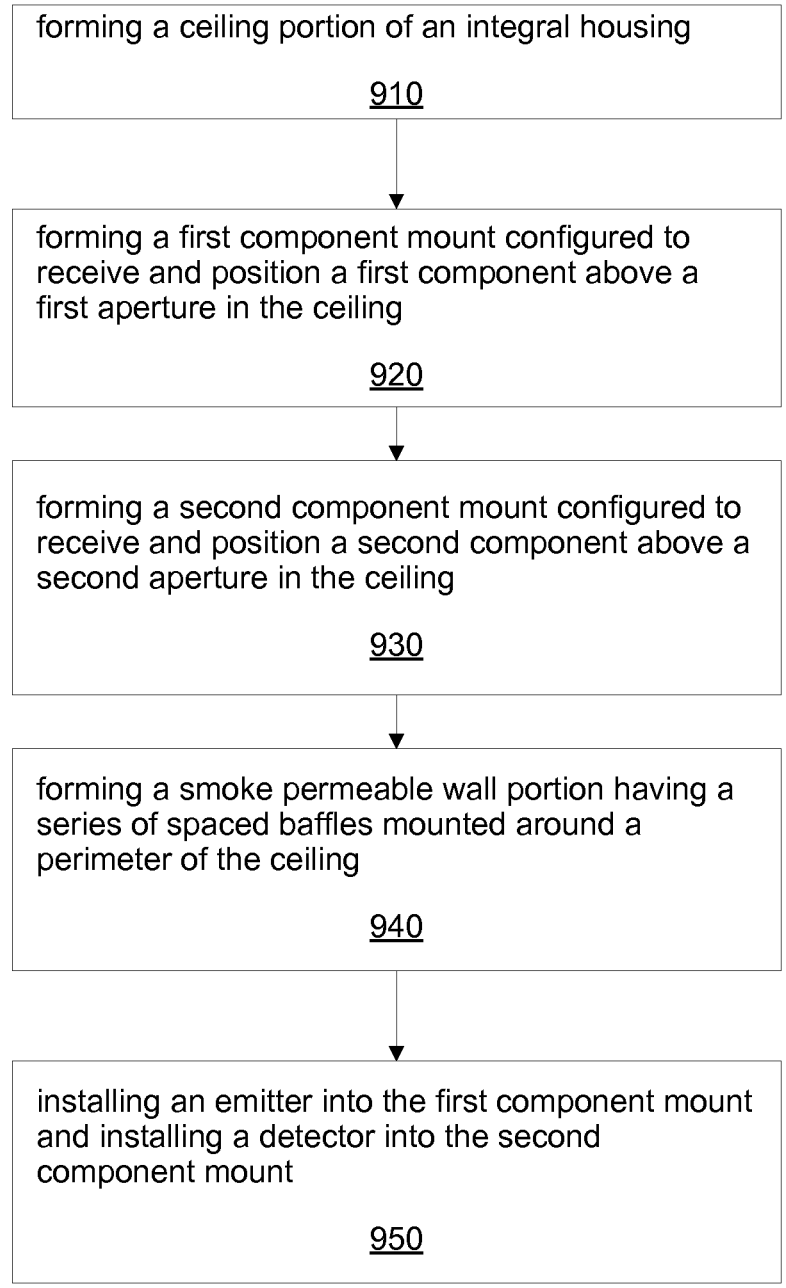
FIG. 9 is a flowchart of an exemplary method for manufacturing an integrated smoke cell.

FIG. 9 is a flowchart of an exemplary embodiment of a method for manufacturing an integrated smoke cell. It should be noted that any process descriptions or blocks in flow charts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

As shown by block 910, the method includes forming a ceiling portion of an integral housing. A step includes forming a first component mount configured to receive and position a first component above a first aperture formed in the ceiling, as shown by block 920. A step includes forming a second component mount configured to receive and position a second component above a second aperture formed in the ceiling, as shown by block 930.

A smoke permeable wall having a series of baffles mounted around the perimeter of the ceiling is formed, as shown by block 940. The forming of the ceiling, wall and component mounts is preferably done by injection molding of a material, for example, plastic, into a shaped mold. An emitter is installed into the first component mount, and a detector is installed into the second component mount, as shown by block 950.

System

Figure 10:
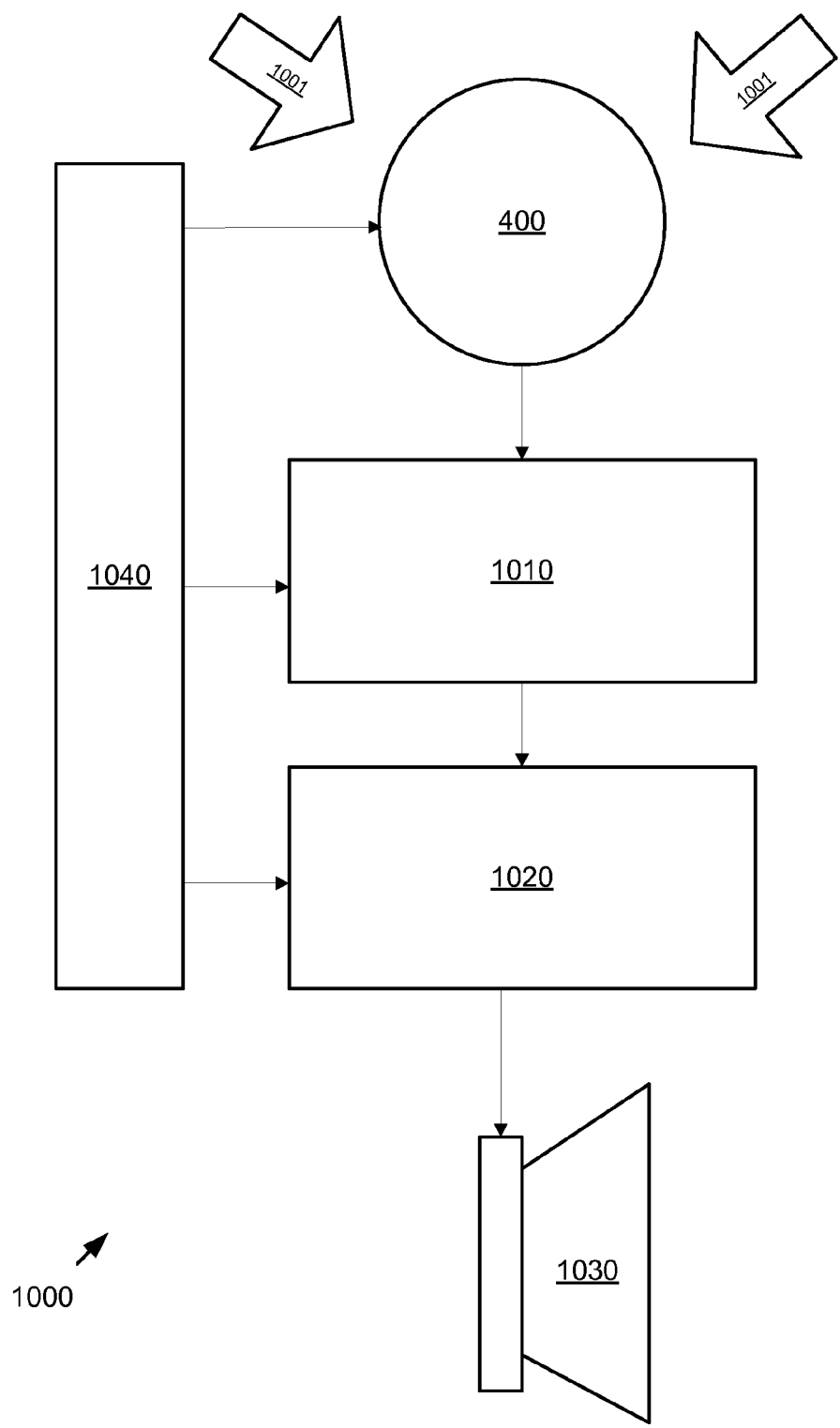
FIG. 10 is a schematic diagram of a smoke detector system incorporating the integrated smoke cell of the current invention.

FIG. 10 is a schematic diagram of an exemplary smoke detector system 1000 including an integrated smoke cell. The integrated smoke cell may be the smoke cell 400 of the first embodiment having a single ceiling mounted emitter and a single ceiling mounted detector, or it may be the smoke cell 800 (FIG. 8) of the second embodiment having multiple ceiling mounted emitters and/or detectors. The smoke cell detector provides a signal to a sensor circuit 1010. When smoke 1001 enters the smoke cell 400, the sensor circuit 1010 determines the level of smoke 1001 present in the smoke cell 400 based on the signal provided by the smoke cell detector to the sensor circuit 1010. The sensor circuit 1010 may include a logic circuit, for example, including a microprocessor and storage for instructions for the microprocessor with threshold levels configuring the sensor circuit to determine when smoke 1001 is present in the smoke cell 400. Upon sensing smoke 1001, the sensor circuit 1010 provides a trigger signal to an alarm circuit 1020 that activates an alarm mechanism, for example a speaker/oscillator 1030, or a visual alert mechanism such as a strobe light (not shown). The components 400, 1010, 1020, 1030 may be powered by a power supply 1040, for example, a wired power supply or a battery. Of course, this is just one example of a smoke detector system, and persons having ordinary skill in the art will readily understand how the smoke cell 400 may be used in other variations of smoke detector systems.

Figure 11:
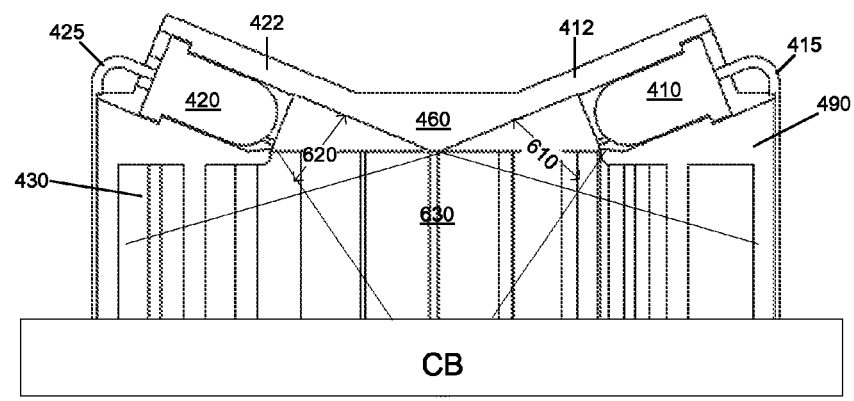
FIG. 11 is a schematic diagram of the integrated smoke cell in FIG. 6 attached to a circuit board.

FIG. 11 is a schematic diagram of the integrated smoke cell in FIG. 6 attached to a circuit board. The circuit board is labeled "CB." All of the other reference numerals in FIG. 11 were discussed above with reference to FIG. 6.

An integral one piece housing for a smoke cell may be advantageous over composite housings. For example, an integral housing may be more stable. An integral housing may simplify ensuring alignment between the emitter and detector, and alignment of the interference zone within the chamber than housings formed of two or more pieces. Similarly, a one piece housing may simplify the manufacturing process of mounting the housing to a PCB, thus reducing manufacturing cost, and facilitating, for example, automated assembly on a smoke detector board and testing within the manufacturing process.

It will be apparent to those skilled in the art that various modifications and variations can be made to the structure of the present invention without departing from the scope or spirit of the invention. For example, in a third exemplary embodiment, a smoke cell may have a floor portion mounted upon a printed circuit board, where the integrated smoke cell having a wall and ceiling are mounted upon the floor portion. The floor portion may be treated to absorb, disperse, and/or reflect light in a desired manner. For example, it may be desirable for the floor portion to absorb light from an emitter mounted in the ceiling of the integrated smoke cell. In view of the foregoing, it is intended that the present invention cover modifications and variations of this invention provided they fall within the scope of the following claims and their equivalents.

What is claimed is:

1. An integrated smoke cell comprising:
  an integral housing comprising a ceiling portion and a smoke permeable wall portion,
  a circuit board mounted to the integral housing;
  a smoke chamber within the integral housing and bounded to the ceiling portion, the smoke permeable wall portion and the circuit board;
  an emitter mounted substantially above a first aperture in said ceiling portion;
  an emitting region adjacent to said emitter within said chamber;
  a detector mounted substantially above a second aperture in said ceiling portion; and
  a detecting region adjacent to said detector within said smoke chamber,
  wherein the detecting region at least partially intersects the emitting region in the smoke chamber, and wherein said emitter and detector are disposed substantially outside said smoke chamber.

2. The integrated smoke cell of claim 1, wherein said integral housing is configured to mount to said circuit board, and said circuit board forms a floor of said chamber,
  wherein said floor of said chamber is opposite said ceiling portion of said smoke chamber, and
  wherein the detecting region at least partially intersects the emitting region between the said floor and said ceiling portion.

3. The integrated smoke cell of claim 1, wherein said housing is configured to mount to said circuit board using a surface mount device technique.

4. The integrated smoke cell of claim 1, wherein said smoke permeable wall portion comprises a plurality of baffles disposed adjacent to said ceiling,
  wherein said baffles are spaced apart to allow ingress of smoke into said smoke chamber and to obstruct ingress of light into said smoke chamber.

5. The integrated smoke cell of claim 4, wherein each of said baffles has a substantially chevron shaped profile.

6. The integrated smoke cell of claim 4, wherein at least one of said plurality of baffles comprises a guide feature configured to position said housing against said circuit board.

7. The integrated smoke cell of claim 4, wherein each of said baffles has a substantially lambda shaped profile.

8. The integrated smoke cell of claim 1, wherein said smoke permeable wall portion has a substantially circular cross section.

9. The integrated smoke cell of claim 8, wherein said emitter and said detector are diametrically opposed in position across said substantially circular cross section.

10. The integrated smoke cell of claim 1, wherein said ceiling portion comprises an interior surface, wherein said interior surface is treated to disperse light in a predetermined fashion.

11. The integrated smoke cell of claim 1, wherein:
  said emitter is disposed at a first angle with respect to an exterior surface of said ceiling; and
  said detector is disposed at a second angle with respect to said exterior surface.

12. The integrated smoke cell of claim 11, wherein said first angle is substantially equal to said second angle.

13. The integrated smoke cell of claim 1, further comprising:
  an emitter mount for said emitter formed in said ceiling portion; and
  a detector mount for said detector formed in said ceiling portion.

14. The integrated smoke cell of claim 1, wherein the circuit board and the ceiling portion are on opposite sides of where the detecting region and the emitting region at least partially intersect in the smoke chamber.

15. The integrated smoke cell of claim 1, further comprising:
- electrical detector leads that extend from the detector, through the integral housing and to the circuit board; and
- electrical emitter leads that extend from the emitter, through the integral housing and to the circuit board,
- wherein the smoke permeable wall portion of the integral housing has a modified baffle in proximity to the electrical detector leads and/or the electrical emitter leads,
- wherein each modified baffle is configured to secure one or more of the electrical leads within holes, slots, or ridges in the modified baffle to minimize obstruction of airflow by the electrical detector leads or the electrical emitter leads into the smoke chamber.

16. A smoke cell configured to be mounted on a circuit board comprising:
- an integral housing comprising a ceiling portion and a wall portion,
- a circuit board mounted to the integral housing;
- a smoke chamber within the integral housing and bounded by the ceiling portion, the wall portion and the circuit board,
- said wall portion comprising a plurality of spaced baffles disposed adjacent to said ceiling portion;
- a first emitter mounted substantially above a first emitter aperture in said ceiling portion;
- a second emitter mounted substantially above a second emitter aperture in said ceiling portion; and
- a first detector mounted substantially above a first detector aperture in said ceiling portion,
- wherein said first emitter, said second emitter and said first detector are disposed substantially outside said smoke chamber.

17. The smoke cell of claim 16, wherein said circuit board forms a floor of said smoke chamber.

18. The smoke cell of claim 16, further comprising a second detector mounted substantially above a second detector aperture in said ceiling portion,
- wherein said second detector is disposed substantially outside said smoke chamber.

19. The smoke cell of claim 16, further comprising a floor disposed adjacent to said wall portion and opposite said ceiling portion of said integral housing, and disposed adjacent to said circuit board.

20. The smoke cell of claim 19, wherein said floor is treated to disperse light in a predetermined fashion.

* * * * *